(12) United States Patent
Uckun

(10) Patent No.: US 6,635,651 B2
(45) Date of Patent: Oct. 21, 2003

(54) INHIBITORS OF THROMBIN INDUCED PLATELET AGGREGATION

(75) Inventor: Faith M. Uckun, White Bear Lake, MN (US)

(73) Assignee: Parker Hughes Institute, St. Paul, MN (US)

( * ) Notice: Subject to any disclaimer, the term of this patent is extended or adjusted under 35 U.S.C. 154(b) by 32 days.

(21) Appl. No.: 10/157,474

(22) Filed: May 28, 2002

(65) Prior Publication Data

US 2003/0013728 A1 Jan. 16, 2003

Related U.S. Application Data

(63) Continuation of application No. PCT/US00/42345, filed on Nov. 29, 2000.
(60) Provisional application No. 60/168,179, filed on Nov. 30, 1999.

(51) Int. Cl.[7] .............................................. A61K 31/517
(52) U.S. Cl. ................ 514/266.4; 514/266.1; 514/266.3
(58) Field of Search ........................... 514/266.1, 266.4, 514/266.3, 259

(56) References Cited

U.S. PATENT DOCUMENTS

| | | | |
|---|---|---|---|
| 3,800,039 A | 3/1974 | Marquis et al. | 424/251 |
| 5,436,233 A | 7/1995 | Lee et al. | 514/63 |
| 5,962,458 A | 10/1999 | Lohmann et al. | 514/259 |
| 6,080,747 A * | 6/2000 | Uckun et al. | 514/266.1 |
| 6,177,433 B1 | 1/2001 | Uckun et al. | 514/259 |
| 6,265,160 B1 * | 7/2001 | Leonard | 435/6 |
| 6,313,130 B1 * | 11/2001 | Uckun et al. | 514/266.24 |
| 6,452,005 B1 | 9/2002 | Uckun et al. | 544/293 |

FOREIGN PATENT DOCUMENTS

WO 97/32856 9/1997

OTHER PUBLICATIONS

Sudbeck et al., Jun. 1999, *Clinical Cancer Research*, vol. 5, pp. 1569–1582.

Tibbles, et al, "Prevention of Fatal Thromboembolism In Mice by Selectively Targeting Jak 3 Kinase In Platelets With 4–(4'hydroxyphenyl)–Amino–6,7–Dimethoxyquinazoline"; Blood, vol. 96. No. 11 part 1, Nov. 16, 2000 (2000–116), p. 273a XP002174855.

Trieu, et al, "*Treatment of Atherosclerosis In Apolipoprotein E–Deficient Mice with 4–(3'–Bromobenzoyl)–6, 7–Dimethoxyquinazoli Ne (WHI–P164), A Potent Inhibitor of Triglyceride Synthesis*", J. Cardiovasc. Pharmacol, (2000), 35 (2), 179–188. XP001013470.

Kalmes, et al, "*Heparin Blockade of Thrombin–Induced Smooth Muscle Cell Migration Involve Inhibition of Epidermal Growth Factor (EGF) Receptor Transactivation By Heparin–Binding EGF–Like Growth Factor*", Circulation Research, (Jul. 21, 2000), 87 (2) 92–8. XP001013472.

Trieu, et al, "A Specific Inhibitor of Janus Kinase–3 Increases Survival In A Transgenic Mouse Model of Amyotrophic Lateral Sclerosis", Biochem Biophys. Res. Commun. (2000), 267(3). 22–25. XP001018912.

Chen, et al, "*Pharmacokinetics and Biologic Activity of The Novel Mast Cell Inhibitor, 4–(3'–Hydroxyphenyl)–Amino–6, 7–Dimethoxyqu Inazoline In Mice*", Pharm. Res. (1999), 16(1), 117–122, XP000937666.

* cited by examiner

Primary Examiner—Dwayne C Jones
(74) Attorney, Agent, or Firm—Merchant & Gould P.C.

(57) ABSTRACT

The present invention describes a therapeutic method useful for treating or preventing a condition of platelet aggregation in a subject including administering a pharmaceutically effective amount of a compound or composition that inhibits JAK-3 and/or tyrosine phosphorylation of STAT-3 and inhibits thrombin induced platelet aggregation. The condition of platelet aggregation includes hematopoietic and cerbrovascular diseases.

7 Claims, 2 Drawing Sheets

INHIBITORS OF THROMBIN INDUCED PLATELET AGGREGATION

PRIORITY OF THE INVENTION

This application is a continuation of PCT/US00/42345, filed on Nov. 29, 2000, published in English on Jun. 28, 2001 as WO 01/45641, and designating the United States, which claims benefit of U.S. Provisional Application Nos. 60/168,179, filed on Nov. 30, 1999.

FIELD OF THE INVENTION

The present invention relates to a therapeutic method for treating or preventing a disease or condition of platelet aggregation in a subject wherein the method includes administering a pharmaceutically effective amount of a compound that inhibits platelet aggregation and specifically, thrombin induced platelet aggregation.

BACKGROUND OF THE INVENTION

Heart disease, a common cause of death in today's society, is often a result of ischemic syndromes that are produced by atherosclerosis and arteriosclerosis including myocardial infarction, chronic unstable angina, transient ischemic attacks and strokes, peripheral vascular disease, arterial thrombosis, preeclampsia, embolism, restenosis and/or thrombosis following angioplasty, carotid endarterectomy, anastomosis of vascular grafts, and other cardiovascular devices. These syndromes represent a variety of stenotic and occlusive vascular disorders thought to be initiated by platelet aggregation on vessel walls or within the lumen by blood-born mediators thereby forming thrombin that restrict blood flow.

The basic mechanism of platelet aggregation has been well-studied. The mechanism starts with a blood vessel injury such as narrowing of the lumen, plaque formation, and the presence of foreign bodies/medical instruments. This injury leads to platelet activation and binding of fibrinogen and ligands. Upon ligand binding, the JAK (Janus-family Kinase) kinases, a family of cytoplasmic protein tyrosine kinases which mediate cytokine receptor signaling, undergo tyrosine phosphorylation and activate the cytoplasmic latent forms of the STAT family transcription factors (Signal Transducers and Activators of Transcription). In an investigation of platelet aggregation in mice deficient in JAK-3, which maps to human chromosome 19p12–13.1, a decrease in thrombin-induced platelet aggregation was discovered by the Applicant.

Gelotte, U.S. Pat. No. 5,972,967 and Scarborough, et al. U.S. Pat. No. 5,968,902 have described certain compounds and compositions that inhibit binding to a platelet by limiting the binding of fibrinogen. Nevertheless, there sill is a need for finding compounds and improved methods to treat or prevent a condition of platelet aggregation.

SUMMARY OF THE INVENTION

In accordance with the purpose(s) of this invention, as embodied and broadly described herein, this invention, in ore aspect, relates to a therapeutic method for treating or preventing a disease or condition of platelet aggregation in a subject including administering a pharmaceutically effective amount of a compound or composition that inhibits platelet aggregation and specifically, thrombin induced platelet aggregation.

In a second aspect, the invention relates to a method for treating or preventing a disease or condition of platelet aggregation in a subject by administering a pharmaceutically effective amount of a compound represented by formula (I):

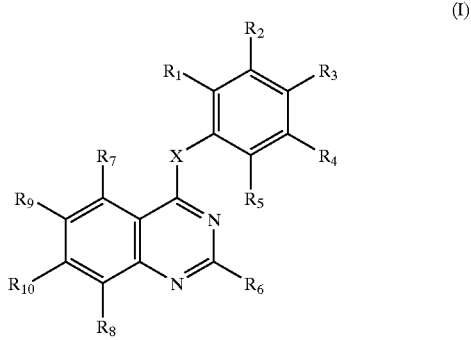

(I)

wherein:
X is selected from the group consisting of HN, $R_{11}N$, S, O, $CH_2$, and $R_{11}CH$;
$R_{11}$ is $(C_1-C_4)$alkyl or $(C_1-C_4)$alkanoyl;
$R_1-R_5$ are each independently selected from the group consisting of hydrogen, hydroxy, and halo where at least one of $R_1-R_5$ is hydroxy;
$R_6$, $R_7$, and $R_8$ are each independently selected from the group consisting of hydrogen, hydroxy, mercapto, amino, nitro, $(C_1-C_4)$alkyl, $(C_1-C_4)$alkoxy, $(C_1-C_4)$alkylthio, and halo; and
$R_9$ and $R_{10}$ are each independently selected from the group consisting of hydrogen, $(C_1-C_4)$alkyl, $(C_1-C_4)$alkoxy, halo, and $(C_1-C_4)$alkanoyl; or
$R_9$ and $R_{10}$ together are methylenedioxy; or a pharmaceutically acceptable salt thereof.

In another aspect, the invention relates to a method for treating or preventing a disease or condition of platelet aggregation in a subject by administering a pharmaceutically effective amount of a compound represented by formula (II):

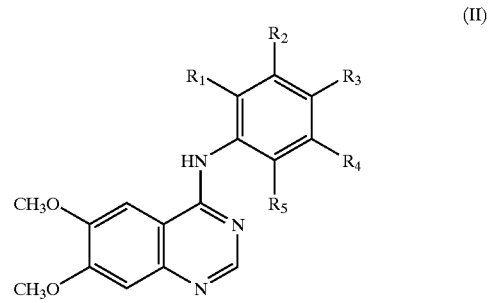

(II)

wherein:
$R_1-R_5$ are each independently selected from the group consisting of hydrogen, hydroxy, and halo where at least one of $R_1-R_5$ is hydroxy; and
a pharmaceutically acceptable salt thereof.

Additional advantages of the invention will be set forth in part in the description which follows, and in part will be obvious from the description, or may be learned by practice of the invention as herein described. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

The accompanying drawings, which are incorporated in and constitute a part of this specification, illustrate several experimental examples and together with the description, serve to explain the principles of the invention

DESCRIPTION OF THE PREFERRED EMBODIMENTS

Figure 1A:
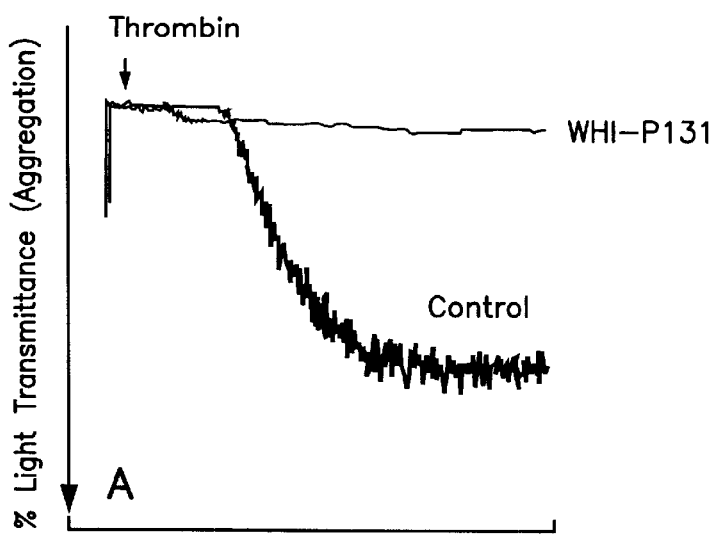
FIGS. 1a, 1b, and 1c are graphs showing reduced thrombin-induced (FIG. 1a) but not collagen-induced (FIG. 1b) platelet aggregation for cells treated with WHI-P131, and reduced thrombin-induced (FIG. 1c) platelet aggregation for cells treated with WHI-P258 (results of Example 4).

The present invention may be understood more readily by reference to the following detailed description of embodiments and preferred embodiments of the invention, and the Examples included therein and to the Figures and their previous and following description.

In this specification and in the claims that follow, reference will be made to a number of terms that shall be defined to have the following meanings:

Reference in the specification and concluding claims to parts by weight of a particular component in a composition, denotes the weight relationship between the component and any other components in the composition for which a part by weight is expressed.

The term "halogen" or "halo" refers to bromine, chlorine, fluorine, and iodine.

The term "alkyl" as used herein refers to a branched or unbranched saturated hydrocarbon group, such as methyl, ethyl, n-propyl, isopropyl, n-butyl, isobutyl, t-butyl, octyl, decyl, tetradecyl, hexadecyl, eicosyl, tetracosyl and the like. The alkyl group may have one or more hydrogen atoms replaced with a functional group. The term "cycloalkane" as used herein refers to a cyclic alkane group.

The term "alkoxy" as used herein intends an alkyl group bound through a single, terminal ether linkage; that is, an "alkoxy" group may be defined as —OR where R is alkyl as defined above. An "alkylthio" group intends an alkyl group bound through a sulfur linkage such as —SR where R is alkyl as defined above.

The term "alkanoyl" as used herein refers to a branched or unbranched acyl group, a carbonyl group with an alkyl group attached. The general formula for alkanoyl is R—CO— wherein the carbon atom is linked to the compound. Example alkanoyls include methanoyl (formyl), ethanoyl (acetyl), propanoyl, and benzoyl.

The term "mercapto" as used herein refers to an —SH group. "Amino" refers to a —NH$_2$ group, and nitro refers to a NO$_2$ group.

As used herein, the term "STAT-3" means signal transducers and activators of transcription (STAT) that associate with JAK-3, including STAT-3α (p92) and STAT-3β (p83) isoforms.

By "platelet aggregation" is meant the clumping together of platelets or red blood cells. As used herein, "inhibiting platelet aggregation" includes slowing platelet aggregation, as well as completely eliminating and/or preventing platelet aggregation. Additionally, "inhibiting platelet function" includes decreasing platelet function, as well as completely eliminating and/or preventing the platelet function. Conditions of platelet aggregation include, but are not limited to, embolus formation, thrombolytic complications, disseminated intravascular comgelopathy, thrombosis, coronary heart disease, thromboembolic complications, myocardial infarction, restenosis, and atrial thrombosis formation in atrial fibrillation, chronic unstable angina, transient ischemic attacks and strokes, peripheral vascular disease, arterial thrombosis, preeclampsia, embolism, restenosis and/or thrombosis following angioplasty, carotid endarterectomy, anastomosis of vascular grafts, and chronic exposure to cardiovascular devices. Such conditions may also result from thromboembolism and reocculsion during and after thermbolytid therapy, after angioplasty, and after coronary artery bypass.

"Thrombin induced platelet aggregation" includes platelet aggregation in response to the enzyme thrombin, which is formed in blood from prothrombin. "Collagen induced platelet aggregation" includes platelet aggregation in response to the protein collagen.

As used throughout, by "contacting" is meant an instance of exposure of at least one cell (e.g., a neural cell, a stem cell, a cardiac cell) to an agent (e.g., a compound that inhibits platelet aggregation and specifically, thrombin induced platelet aggregation).

The term "subject" is meant an individual. Preferably, the subject is a mammal such as a primate, and more preferably, a human. Thus, the "subject" can include domesticated animals (e.g., cats, dogs, etc.), livestock (e.g., cattle, horses, pigs, sheep, goats, etc.), and laboratory animals (e.g., mouse, rabbit, rat, guinea pig, etc.).

In general, "pharmaceutically effective amount" or "pharmaceutically effective dose" means the amount needed to achieve the desired result or results (treating or preventing platelet aggregation). One of ordinary skill in the art will recognize that the potency and, therefore a "pharmaceutically effective amount" can vary for the various compounds that inhibit platelet aggregation and specifically, thrombin induced platelet aggregation used in the invention. One skilled in the art can readily assess the potency of the compounds.

By "pharmaceutically acceptable" is meant a material that is not biologically or otherwise undesirable, i.e., the material may be administered to an individual along with the selected compounds without causing any undesirable biological effects or interacting in a deleterious manner with any of the other components of the pharmaceutical composition in which it is contained.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. The reaction is conducted in water, alone or in combination with an inert, water-miscible organic solvent, at a temperature of from about 0° C. to 100° C., preferably at room temperature. The molar ratio of the compound that inhibits platelet aggregation and specifically, thrombin induced platelet aggregation, to base used are chosen to provide the ratio desired for any particular salts. For preparing, for example, the ammonium salts of the free acid starting material, a particular preferred embodiment, the starting material can be treated with approximately one equivalent of base to yield a salt. When calcium salts are prepared, approximately one-half a molar equivalent of base is used to yield a neutral salt, while for aluminum slats, approximately one-third a molar equivalent of base will be used.

Ester derivatives are typically prepared as precursors to the acid form of the compounds, and accordingly may serve as prodrugs. Generally, these derivatives will be alkyl esters such as methyl, ethyl, and the like. Amide derivatives —(CO)NH$_2$, —(CO)NHR and —(CO)NR$_2$, where R is alkyl, may be prepared by reaction of the carboxylic acid-containing compound with ammonia or a substituted amine.

Specific values listed below for radicals, substituents, and ranges, are for illustration only; they do not exclude other defined values or other values within defined ranges for the radicals and substituents.

Preferred constituents of $R_1$–$R_5$ for the compounds of formula I are independently hydrogen, hydroxy, and halo with at least one of $R_1$–$R_5$ being hydroxy; and preferred constituents of $R_6$, $R_7$, and $R_8$ are each independently selected from the group consisting of hydrogen, hydroxy, mercapto, amino, nitro, $(C_1$–$C_4)$alkyl, $(C_1$–$C_4)$alkoxy, $(C_1$–$C_4)$alkylthio, and halo; more preferably, $R_6$, $R_7$, and $R_8$ are each hydrogen.

Preferably, $R_9$ and $R_{10}$ are each independently selected from the group consisting of hydrogen, $(C_1$–$C_4)$alkyl, $(C_1$–$C_4)$alkoxy, halo, and $(C_1$–$C_4)$alkanoyl; or $R_9$ and $R_{10}$ together are methylenedioxy; more preferably $R_9$ and $R_{10}$ are each OCH$_3$.

Preferred constituents of X are HN, $R_{11}$N, S, O, CH$_2$, and $R_{11}$CH; wherein $R_{11}$ is preferably $(C_1$–$C_4)$alkyl or $(C_1$–$C_4)$ alkanoyl; more preferably X is HN.

Some exemplary compounds of the invention are listed below with their characterization data:

4-(3',5'-Dibromo-4'-hydroxyphenyl)-amino-6,7-dimethoxyquinazoline [WHI-P97]

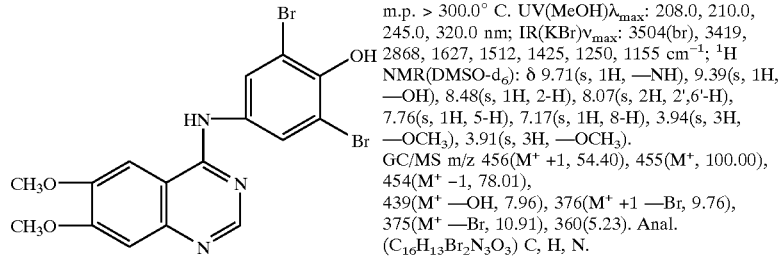

m.p. > 300.0° C. UV(MeOH)$\lambda_{max}$: 208.0, 210.0, 245.0, 320.0 nm; IR(KBr)$\nu_{max}$: 3504(br), 3419, 2868, 1627, 1512, 1425, 1250, 1155 cm$^{-1}$; $^1$H NMR(DMSO-d$_6$): δ 9.71(s, 1H, —NH), 9.39(s, 1H, —OH), 8.48(s, 1H, 2-H), 8.07(s, 2H, 2',6'-H), 7.76(s, 1H, 5-H), 7.17(s, 1H, 8-H), 3.94(s, 3H, —OCH$_3$), 3.91(s, 3H, —OCH$_3$). GC/MS m/z 456(M$^+$ +1, 54.40), 455(M$^+$, 100.00), 454(M$^+$ −1, 78.01), 439(M$^+$ —OH, 7.96), 376(M$^+$ +1 —Br, 9.76), 375(M$^+$ —Br, 10.91), 360(5.23). Anal. ($C_{16}H_{13}Br_2N_3O_3$) C, H, N.

4-(4'-Hydroxyphenyl)-amino-6,7-dimethoxyquinazoline [WHI-P131]

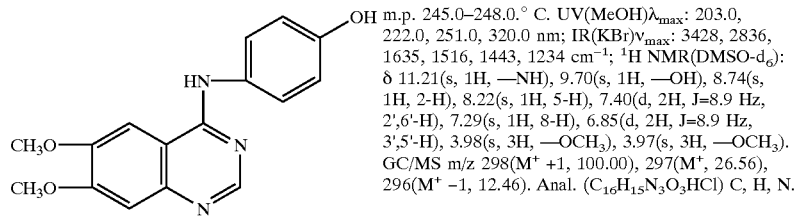

m.p. 245.0–248.0.° C. UV(MeOH)$\lambda_{max}$: 203.0, 222.0, 251.0, 320.0 nm; IR(KBr)$\nu_{max}$: 3428, 2836, 1635, 1516, 1443, 1234 cm$^{-1}$; $^1$H NMR(DMSO-d$_6$): δ 11.21(s, 1H, —NH), 9.70(s, 1H, —OH), 8.74(s, 1H, 2-H), 8.22(s, 1H, 5-H), 7.40(d, 2H, J=8.9 Hz, 2',6'-H), 7.29(s, 1H, 8-H), 6.85(d, 2H, J=8.9 Hz, 3',5'-H), 3.98(s, 3H, —OCH$_3$), 3.97(s, 3H, —OCH$_3$). GC/MS m/z 298(M$^+$ +1, 100.00), 297(M$^+$, 26.56), 296(M$^+$ −1, 12.46). Anal. ($C_{16}H_{15}N_3O_3$HCl) C, H, N.

4-(3'-Bromo-4'-hydroxyphenyl)-amino-6,7-dimethoxyquinazoline [WHI-P154]

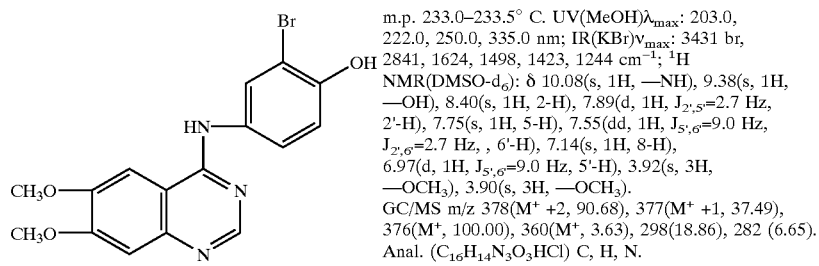

m.p. 233.0–233.5° C. UV(MeOH)$\lambda_{max}$: 203.0, 222.0, 250.0, 335.0 nm; IR(KBr)$\nu_{max}$: 3431 br, 2841, 1624, 1498, 1423, 1244 cm$^{-1}$; $^1$H NMR(DMSO-d$_6$): δ 10.08(s, 1H, —NH), 9.38(s, 1H, —OH), 8.40(s, 1H, 2-H), 7.89(d, 1H, $J_{2',5'}$=2.7 Hz, 2'-H), 7.75(s, 1H, 5-H), 7.55(dd, 1H, $J_{5',6'}$=9.0 Hz, $J_{2',6'}$=2.7 Hz, , 6'-H), 7.14(s, 1H, 8-H), 6.97(d, 1H, $J_{5',6'}$=9.0 Hz, 5'-H), 3.92(s, 3H, —OCH$_3$), 3.90(s, 3H, —OCH$_3$). GC/MS m/z 378(M$^+$ +2, 90.68), 377(M$^+$ +1, 37.49), 376(M$^+$, 100.00), 360(M$^+$, 3.63), 298(18.86), 282 (6.65). Anal. ($C_{16}H_{14}N_3O_3$HCl) C, H, N.

-continued

4-(3'-Hydroxyphenyl)-amino-6,7-dimethoxyquinazoline [WHI-P180]

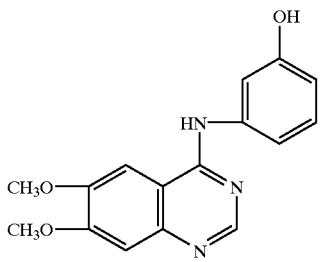

m.p. 256.0–258.0° C. $^1$HNMR(DMSO-d$_6$): δ 9.41(s, 1H, —NH), 9.36(s, 1H, —OH), 8.46(s, 1H, 2-H), 7.84(s, 1H, 5-H), 7.84–6.50(m, 4H, 2', 4', 5', 6'-H), 7.20(s, 1H, 8-H), 3.96(s, 3H, —OCH$_3$), 3.93(s, 3H, —OCH$_3$). UV(MeOH)λ$_{max}$(ε): 204.0, 224.0, 252.0, 335.0 nm. IR(KBr)ν$_{max}$: 3394, 2836, 1626, 1508, 1429, 1251 cm$^{-1}$. GM/MS m/z: 297(M$^+$, 61.89), 296(M$^+$, 61.89), 296(M$^+$ −1, 100.00), 280(M$^+$ —OH, 13.63). Anal. (C$_{16}$H$_{15}$N$_3$O$_3$·HCl) C, H, N.

A preferred compound for use in the present invention is 4-(4'-hydroxyphenyl)amino-6,7-dimethoxyquinazoline,

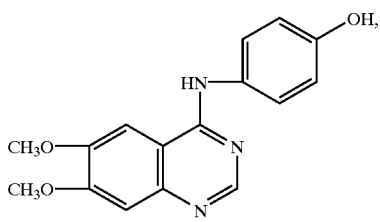

or a pharmaceutically acceptable salt thereof.

Pharmaceutically acceptable salts of 4-(4'-hydroxyphenyl)amino-6,7-dimethoxyquinazoline, or any other compound useful in the present invention, may be used in the present invention. Examples of acceptable salts are organic acid addition salts formed with acids, which form a physiological acceptable anion, including, but not limited to, tosylate, methanesulfonate, acetate, citrate, malonate, tartarate, succinate, benzoate, ascorbate, α-ketoglutarate, and α-glycerophosphate. Suitable inorganic salts may also be formed, including, but not limited to, hydrochloride, sulfate, nitrate, bicarbonate, and carbonate salts.

Acceptable salts may be obtained using standard procedures well known in the art, for example by reacting a sufficiently basic compounds such as an amine with a suitable acid affording a physiologically acceptable anion.

Synthetic Methods

The compounds of the present invention may be readily synthesized using techniques generally known to synthetic organic chemists. Suitable experimental methods for making and derivatizing aromatic compounds are described, for example, in U.S. Pat. No. 6,080,748 to Uckun et al., the disclosure of which is hereby incorporated by reference.

Utility and Administration

The therapeutic method included herewith is useful for treating or preventing a condition of platelet aggregation, in a subject comprising administering a pharmaceutically effective amount of a compound or composition that inhibits JAK-3 and/or tyrosine phosphorylation of STAT-3 and that inhibits platelet aggregation, specifically, thrombin induced platelet aggregation.

The condition of platelet aggregation includes hematopoietic and cerbrovascular diseases such as, but not limited to, embolus formation, thrombolytic complications, disseminated intravascular comgelopathy, thrombosis, coronary heart disease, thromboembolic complications, myocardial infarction, restenosis, or atrial thrombosis formation in atrial fibrillation. Such platelet aggregation inhibition may selectively target the thrombin pathway, over other pathways including collagen induced platelet aggregation.

The methods include contacting the cells with such compounds or compositions, or administering to the subject a pharmaceutically effective amount of these compounds or compositions. In one embodiment, the cells are part of the blood and immune system including: red blood cell, megakaryocytes, macrophages (e.g. monocytes, connective tissue macrophages, Langerhans cells, osteoclasts, dendritic cells, microglial cells), neutrophils, eosinophils, basophils, mast cells, T lymphocytes (e.g. helper T cells, suppressor T cells, killer T cells), B lymphocytes (e.g. IgM, IgG, IgA, IgE), killer cell, and stem cells and committed progenitors for the blood and immune system. In another embodiment, the cells are contractile cells such as skeletal muscle cells (e.g. red, white, intermediate, muscle spindle, satellite cells), heart muscle cells (e.g. ordinary, nodal, Purkinje fiber), smooth muscle cells, and myoepithelial cells.

It is well known in the art how to determine the inhibition of platelet aggregation using the standard tests described herein, or using other similar tests. Preferably, the method would result in at least a 10% reduction in thrombin-induced platelet aggregation, including, for example, 15%, 20%, 25%, 30%, 40%, 50%, 60%, 70%, 80%, 90%, 100%, or any amount in between, more preferably by 90%. Similarly, the method would result in at least a 10% reduction in thrombin-induced tyrosine phosphorylation of STAT-3β, including, for example, 15%, 20%, 25%, 30%, 40%, 50%, 60%, 70%, 80%, 90%, 100%.

The reduction can be measured, for example, by comparing the optical impedance in a chronology platelet aggregometer. Any other known measurement method may also be used. For example, upon thrombin stimulation, STAT-3β tyrosine phosphorylation increases over time and so the measurement may include measuring JAK-3 and/or STAT-3β tyrosine phosphorylation.

The cells can be contacted in vitro, for example, by adding the compound to the culture medium (by continuous infusion, by bolus delivery, or by changing the medium to a medium that contains the agent) or by adding the agent to the extracellular fluid in vivo (by local delivery, systemic delivery, intravenous injection, bolus delivery, or continuous infusion). The duration of "contact" with a cell or population of cells is determined by the time the compound is present at physiologically effective levels or at presumed physiologically effective levels in the medium or extracellular fluid bathing the cell or cells. Preferably, the duration of contact is 1–96 hours, and more preferably, for 24 hours, but such time would vary based on the half life of the compound and could be optimized by one skilled in the art using routine experimentation.

The compounds useful in the present invention can be formulated as pharmaceutical compositions and administered to a mammalian host, such as a human patient or a domestic animal in a variety of forms adapted to the chosen route of administration, i.e., orally or parenterally, by intravenous, intramuscular, topical or subcutaneous routes.

The compounds of the present invention can also be administered using gene therapy methods of delivery. See, e.g., U.S. Pat. No. 5,399,346, which is incorporated by reference in its entirety. Using a gene therapy method of delivery, primary cells transfected with the gene for the compounds of the present invention can additionally be transfected with tissue specific promoters to target specific organs, tissue, grafts, tumors, or cells.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compounds may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compounds may be incorporated into sustained-release preparations and devices.

The active compounds may also be administered intranasally by inhalation, intravenously or intraperitoneally by infusion or injection. Solutions of the active compounds or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for inhalation, injection, or infusion can include sterile aqueous solutions or dispersions or sterile powders comprising the active ingredient which are adapted for the extemporaneous preparation of sterile inhalation, injectable, or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, hydroxyalkyls or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478),Smith et al. (U.S. Pat. No. 4,559,157) and Wortzman (U.S. Pat. No. 4,820,508).

Useful dosages of the compounds can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The amount of the compounds, or an active salt or derivative thereof, required for use in treatment will vary not only with the particular salt selected but also with the route of administration, the nature of the condition being treated and the age and condition of the patient and will be ultimately at the discretion of the attendant physician or clinician. Also the dosage of the compound varies depending on the target cell, tumor, tissue, graft, or organ.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound may conveniently be administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.0005 to about 300 $\mu$M, preferably, about 0.001 to 100 $\mu$M, more preferably, about 1 to about 100 $\mu$M. This may be achieved, for example, by the intravenous injection of a concentration of the active ingredient, optionally in saline, or orally administered as a bolus. Desirable blood levels may be maintained by continuous infusion to provide about 0.0005–50.0 mg/kg/hr or by intermittent infusions containing about 0.004–150 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

An administration regimen could include long-term, daily treatment. By "long-term" is meant at least two weeks and preferably, several weeks, months, or years of duration. Necessary modifications in this dosage range may be determined by one of ordinary skill in the art using only routine experimentation given the teachings herein. See Remington's Pharmaceutical Sciences (Martin, E. W., ed. 4), Mack Publishing Co., Easton, Pa. The dosage can also be adjusted by the individual physician in the event of any complication.

Experimental

The following examples are put forth so as to provide those of ordinary skill in the art with a complete disclosure and description of how the compounds, compositions, articles, devices, and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric.

EXAMPLE 1

Thrombin (0.1 U/ml) induced platelet aggregation in citrated whole blood from heterozygous and homozygous JAK-3 deficient mice and C57BL/6 wild type mice was measured by optical impedence in a Model 560 Dual Chamber Chronolog Platelet Aggregometer. Platelet aggregation in response to thrombin was reduced by 65%±12% in homozygous JAK-3 mice and by 17%±7% in heterozygous mice as compared to control.

EXAMPLE 2

The JAK-3 immune complexes precipitated with anti-JAK-3 antibodies from Triton-100 lysates of platelets stimulated with 0.1 U/ml thrombin were subjected to immune kinase assays. Additional JAK-3 immune complexes were collected, boiled in 2× SDS reducing sample buffer, fractionated on 8% polyacrylamide gels and transferred to PVDF membranes. The membranes were subjected to western blotting analysis utilizing anti-JAK-3 and anti-phosphorylated tyrosine antibodies. The results indicate that JAK-3 is phosphorylated on tyrosine and is kinase active in resting platelets.

EXAMPLE 3

The JAK-3 immune complexes immunoprecipitated from Triton-100 lysates of platelets treated with 100 $\mu$M WHI-P131 or DMSO and then stimulated with 0.1 U/ml thrombin were subjected to immune kinase assays. Additional JAK-3 immune complexes were collected and boiled in 2× SDS reducing sample buffer, fractionated on 8% polyacrylamide gels, transferred to PVDF membranes, and examined for the presence of JAK-3. The activity index was calculated by comparing the phosphoimager units (PIU) to the density of the protein bands in densitometric scanning units (DSU) as shown in Table 1. The results indicate that JAK-3 kinase activity is significantly reduced by WHI-P131 treatment.

TABLE 1

| Measurement | DMSO 0 secs | DMSO 60 secs | WHI-P131 0 secs | WHI-P131 60 secs |
|---|---|---|---|---|
| PIU | 3619 | 1990 | 668 | 495 |
| DSU | 6140 | 7632 | 6079 | 6520 |
| Activity | 0.59 | 0.35 | 0.11 | 0.06 |

EXAMPLE 4

Platelets treated with 100 $\mu$M WHI-P131 or the parent compound, WHI-P258 (negative control), were stimulated with 0.1 U/ml thrombin or 10 $\mu$g/ml collagen. WHI-P131 is described above, WHI-P258 is an unsubstituted quinazoline and structurally shown below.

| 4-(phenyl)-amino-6,7-dimethoxyquinazoline [WHI-P258] |
|---|
| 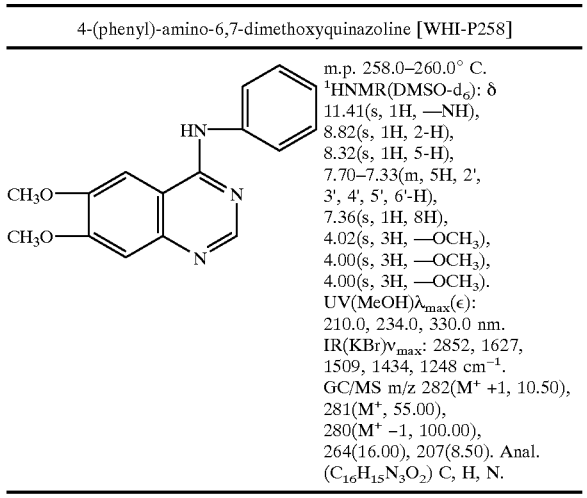 m.p. 258.0–260.0° C.<br>$^1$HNMR(DMSO-$d_6$): δ<br>11.41(s, 1H, —NH),<br>8.82(s, 1H, 2-H),<br>8.32(s, 1H, 5-H),<br>7.70–7.33(m, 5H, 2',<br>3', 4', 5', 6'-H),<br>7.36(s, 1H, 8H),<br>4.02(s, 3H, —OCH$_3$),<br>4.00(s, 3H, —OCH$_3$),<br>4.00(s, 3H, —OCH$_3$).<br>UV(MeOH)$\lambda_{max}$(ε):<br>210.0, 234.0, 330.0 nm.<br>IR(KBr)$v_{max}$: 2852, 1627,<br>1509, 1434, 1248 cm$^{-1}$.<br>GC/MS m/z 282(M$^+$ +1, 10.50),<br>281(M$^+$, 55.00),<br>280(M$^+$ −1, 100.00),<br>264(16.00), 207(8.50). Anal.<br>(C$_{16}$H$_{15}$N$_3$O$_2$) C, H, N. |

Figure 1B:
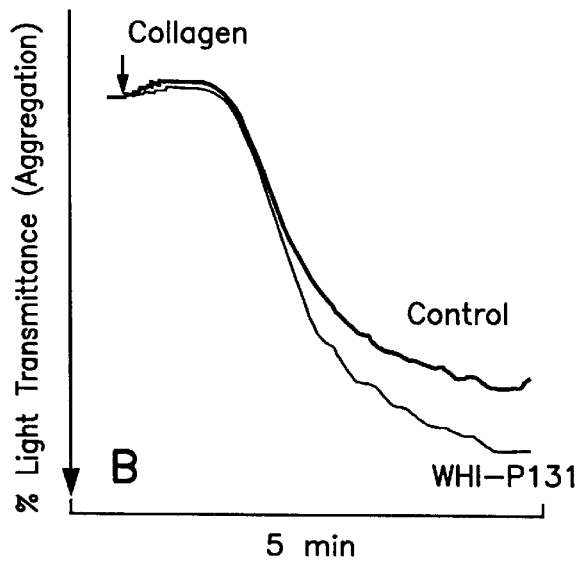
Figure 1C:
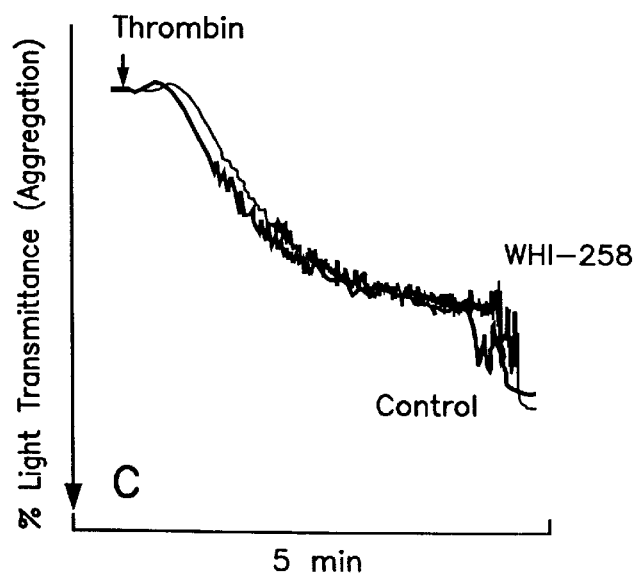

Platelet aggregation with respect to control was monitored in a Chronolog Model 560 Dual Chamber Platelet Aggregometer. WHI-P131 significantly reduced thrombin (as shown in FIG. 1A) but not collagen (shown in FIG. 1B) induced platelet aggregation. WHI-P258 had no effect on the thrombin response (FIG. 1C).

EXAMPLE 5

Figure 2:
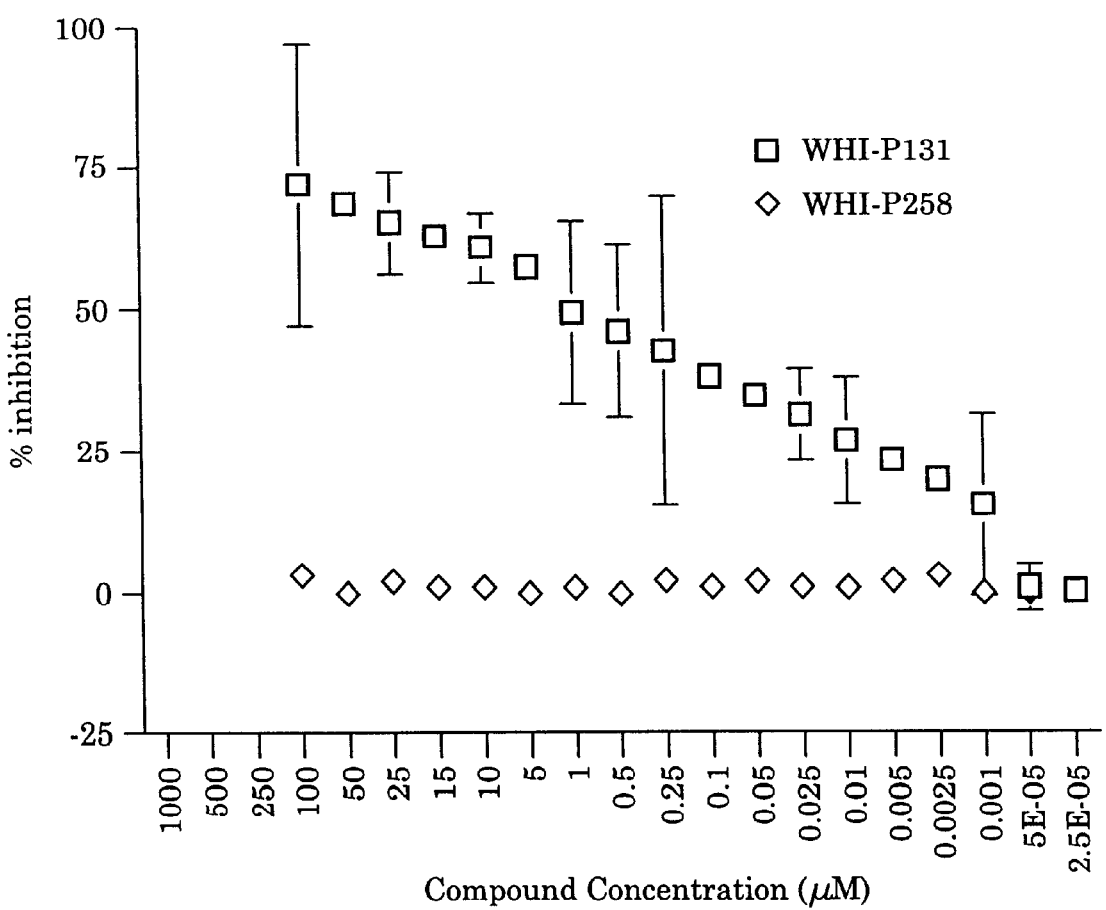
FIG. 2 is a graph showing dose-dependent inhibition of thrombin induced platelet aggregation by WHI-P131 (results of Example 5).

Platelets treated with varying concentrations of WHI-P131 or WHI-P258 (negative control) were stimulated with 0.1 U/ml thrombin. Platelet aggregation with respect to control was monitored in a Chronolog Model 560 Dual Chamber Platelet Aggregometer. WHI-P131 inhibited thrombin-induced platelet aggregation in a dose dependent manner with an IC$_{50}$ value of 1.5 μM. The results are charted in FIG. 2.

EXAMPLE 6

Whole cell lysates from resting platelets and FL8–2 cells (as a positive control) were collected and boiled in 2× SDS reducing sample buffer, fractionated on a 8% polyacrylamide gel and transferred to PVDF membranes. The membranes were subjected to Western blot analysis and examined for the presence of STAT-3α and STAT-3β isoforms. Both isoforms were found to be present in the platelets.

EXAMPLE 7

Whole cell lysates from platelets stimulated with 0.1 U/ml thrombin or 10 μg/ml collagen were collected, boiled in 2× SDS sample buffer, fractionated on an 8% polyacrylamide gel and transferred to PVDF membranes. The membranes were subjected to Western blot analysis utilizing antibodies which recognize all isoforms of STAT-3. The results show that STAT-3β tyrosine phosphorylation increased over time of thrombin stimulation, but not collagen stimulation.

EXAMPLE 8

Whole cell lysates from platelets treated with WHI-P131 or DMSO, stimulated with 0.1 U/ml thrombin or 10 μg/ml collagen were collected and boiled in 2× SDS sample buffer, fractionated on an 8% polyacrylamide gel and transferred to PVDF membranes. The membranes were subjected to Western blot analysis utilizing antibodies which recognize all phosphorylated isoforms of STAT-3 and phosphotyrosine.

WHI-P131 inhibited thrombin induced STAT-3β tyrosine phosphorylation and overall tyrosine phosphorylation.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for treating a disease or condition characterized by platelet aggregation comprising administering a pharmaceutically effective amount of a JAK-3 inhibitor, wherein the YAK-3 inhibitor inhibits tyrosine phosphorylation of STAT-3.

2. A method for selectively inhibiting thrombin-induced platelet aggregation comprising administering to said platelets a JAK-3 inhibitor.

3. A method for selectively inhibiting thrombin-induced platelet aggregation comprising administering to said platelets a JAK-3 inhibitor represented by formula I:

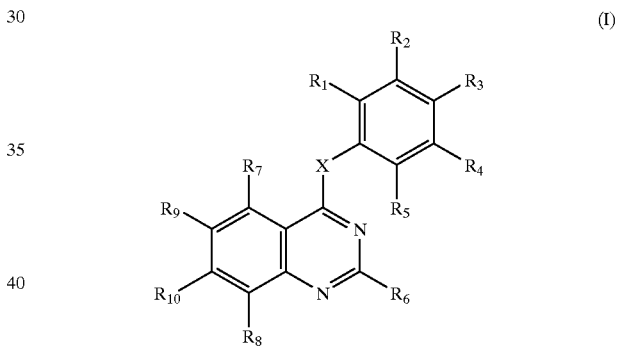

(I)

wherein:
X is selected from the group consisting of HN, R$_{11}$N, S, O, CH$_2$, and R$_{11}$CH;

R$_{11}$ is (C$_1$–C$_4$)alkyl or (C$_1$–C$_4$)alkanoyl;

R$_1$–R$_5$ are each independently selected from the group consisting of hydrogen, hydroxy, and halo where at least one of R$_1$–R$_5$ is hydroxy;

R$_6$, R$_7$, and R$_8$ are each independently selected from the group consisting of hydrogen, hydroxy, mercapto, amino, nitro, (C$_1$–C$_4$)alkyl, (C$_1$–C$_4$)alkoxy, (C$_1$–C$_4$) alkylthio, and halo; and R$_9$ and R$_{10}$ are each independently selected from the group consisting of hydrogen, (C$_1$–C$_4$)alkyl, (C$_1$–C$_4$) alkoxy, halo, and (C$_1$–C$_4$)alkanoyl; or R$_9$ and R$_{10}$ together are methylenedioxy;

or a pharmaceutically acceptable salt thereof.

4. The method of claim 3, wherein X is HN.

5. The method of claim 3, wherein the JAK-3 inhibitor is 94'-hydroxyphenyl)-amino-6,7-dimethoxyquinazoline; 4-(3'5'-dibromo-4'-hydroxyphenyl)-amino-6,7-dimethoxyquinazoline; 4-(3'bromo-4'-hydroxyphenyl)-amino-6,7-dimethoxy-quinazoline; or 4-(3'hydroxyphenyl)-amino-6,7-dimethoxyquinazoline.

6. The method of claim 3, wherein the JAK-3 inhibitor is 4-(4'-hydroxyphenyl)-amino-6,7-dimethoxyquinazoline.

7. The method of claim 1 wherein the condition characterized by platelet aggregation comprises embolus formation, thrombolytic complications, disseminated intravascular comgelopathy, thrombosis, coronary heart disease, thromboembolic complications, myocardial infarction, restenosis, or atrial in atrial fibrillation.

* * * * *

UNITED STATES PATENT AND TRADEMARK OFFICE
CERTIFICATE OF CORRECTION

PATENT NO. : 6,635,651 B2
DATED : October 21, 2003
INVENTOR(S) : Uckun

It is certified that error appears in the above-identified patent and that said Letters Patent is hereby corrected as shown below:

Column 1,
Line 53, "there sill is" should read -- there still is --
Line 60, "ore aspect" should read -- one aspect --

Column 8,
Line 45, "optical impedance in a" should read -- optical impedence in a --

Column 14,
Line 21, "YAK-3" should read -- JAK-3 --
Line 63, "94'-hydroxyphenyl)" should read -- 4-(4'-hydroxyphenyl) --
Line 65, "3'bromo" should read -- (3'-bromo --
Line 66, "3'hydroxyphenyl" should read -- 3'-hydroxyphenyl --

Column 16,
Line 3, "atrial in atrial" should read -- atrial thrombosis formation in atrial --

Signed and Sealed this

Sixteenth Day of March, 2004

JON W. DUDAS
*Acting Director of the United States Patent and Trademark Office*